United States Patent
Gruber (10) Patent No.: US 7,984,989 B2
(45) Date of Patent: *Jul. 26, 2011

(54) RETINAL MELATONIN SUPPRESSOR COMPRISING A FILTER LAYER

(76) Inventor: Jake A. Gruber, Roselle, IL (US)

( * ) Notice: Subject to any disclaimer, the term of this patent is extended or adjusted under 35 U.S.C. 154(b) by 89 days.

This patent is subject to a terminal disclaimer.

(21) Appl. No.: 12/359,841

(22) Filed: Jan. 26, 2009

(65) Prior Publication Data
US 2009/0204186 A1  Aug. 13, 2009

Related U.S. Application Data

(63) Continuation-in-part of application No. 12/115,629, filed on May 6, 2008.

(60) Provisional application No. 61/026,905, filed on Feb. 7, 2008.

(51) Int. Cl.
G02C 7/10 (2006.01)
G02C 7/04 (2006.01)

(52) U.S. Cl. ............ 351/163; 351/44; 351/45; 351/162; 351/165; 351/177

(58) Field of Classification Search ............... 351/41, 351/44, 159, 163, 177
See application file for complete search history.

(56) References Cited

U.S. PATENT DOCUMENTS

| | | | |
|---|---|---|---|
| 4,320,939 A | 3/1982 | Mueller | |
| 4,320,940 A | 3/1982 | Mueller | |
| 4,777,937 A | 10/1988 | Rush et al. | |
| 4,911,166 A | 3/1990 | Leighton et al. | |
| 4,952,046 A | 8/1990 | Stephens et al. | |
| 5,083,858 A | 1/1992 | Girerd | |
| 5,274,403 A | 12/1993 | Gott | |
| 5,343,121 A | 8/1994 | Terman et al. | |
| 5,447,527 A | 9/1995 | Waldman | |
| 5,447,528 A | 9/1995 | Gerardo | |
| 5,592,245 A | 1/1997 | Moore et al. | |

(Continued)

FOREIGN PATENT DOCUMENTS
WO  2004021071 A  11/2004
(Continued)

OTHER PUBLICATIONS

"After Quantum Dots, Now Come Glowing 'Cornell dots,' for biological tagging, imaging and optical computing." Cornell University News Service, http://www.news.cornell.edu/ stories/May05/CUdots.ws.html Apr. 28, 2008.

(Continued)

Primary Examiner — Scott J Sugarman
(74) Attorney, Agent, or Firm — Vedder Price PC (57) ABSTRACT

This disclosure relates to the application of a photoluminescent material with a plurality of nanocrystals, such as quantum dots or Cornell dots, each capable of absorbing electromagnetic energy at a first wavelength and emitting the absorbed energy as a desired wavelength in the direction of a human retina. Preferably, the emitted wavelength is chosen for its ability to suppress naturally occurring melatonin, i.e., blue light. The disclosure also contemplates the placement of the photoluminescent material over the entire surface of a lens or on a portion of the lens to optimize the exposure to the desired wavelength while reducing the overall luminescence. Finally, the photoluminescent material can be applied as a coating, as part of a material applied to the lens, either superficially or in/within the lens, as part of eyewear, or even as an optical treatment system.

29 Claims, 9 Drawing Sheets

U.S. PATENT DOCUMENTS

| | | |
|---|---|---|
| 5,824,024 A | 10/1998 | Dial |
| 6,145,984 A | 11/2000 | Farwig |
| 6,290,713 B1 | 9/2001 | Russell |
| 6,319,273 B1 | 11/2001 | Chen et al. |
| 6,334,680 B1 | 1/2002 | Larson |
| 6,488,698 B1 | 12/2002 | Hyman |
| 6,811,258 B1 | 11/2004 | Grant |
| 6,893,127 B2 | 5/2005 | Reichow et al. |
| 6,913,615 B2 | 7/2005 | Tolkoff et al. |
| 7,015,636 B2 | 3/2006 | Bolta |
| 7,125,416 B2 | 10/2006 | Kent et al. |
| 7,131,990 B2 | 11/2006 | Bansal et al. |
| 7,147,319 B2 | 12/2006 | Lin |
| 7,204,625 B2 | 4/2007 | Wiemers |
| 7,255,435 B2 | 8/2007 | Pratt |
| 7,841,714 B2 * | 11/2010 | Gruber .......................... 351/163 |
| 2003/0030067 A1 * | 2/2003 | Chen .............................. 257/102 |
| 2005/0280769 A1 | 12/2005 | Cano et al. |
| 2007/0298242 A1 | 12/2007 | Huo |

FOREIGN PATENT DOCUMENTS

| | | |
|---|---|---|
| WO | 2004096364 A | 11/2004 |
| WO | 2007103310 A | 9/2007 |

OTHER PUBLICATIONS

"The future of fluorescence. Qdot nanocrystal technology" 2006, Invitrogen Corporation.

"Exciton", Wikipedia, http://en.wikipedia.org/wiki/Excitons. Mar. 24, 2008.

"Optical Coating", Wikipedia, http://en.wikipedia.org/wiki/Optical_coating Mar. 28, 2008.

"Qdot Nanocrystals, The Vision of Nanotechnology", www.probes.invitrogen.com/products/qdot. Mar. 24, 2008.

"EviDot Semiconductor Nanocrystals", http://www.oceanoptics.com/products/evidots.asp Mar. 28, 2008.

"Quantum dot", Wikipedia, http://en.wikipedia.org/wiki/Quantum_dot, Mar. 24, 2008.

"Light Therapy", Wikipedia, http://en.wikipedia.org/wiki/Phototherapy Apr. 21, 2008.

"Bright and Stable Core—Shell Fluorescent Silica Nanoparticles", Hooisweng Ow, et al. 2005 American Chemical Society, Nano Letters, 2005, vol. 5, No. 1, pp. 113-117.

International Search Report issued May 8, 2009 in PCT/US2009/033184.

* cited by examiner

RETINAL MELATONIN SUPPRESSOR COMPRISING A FILTER LAYER

CROSS-REFERENCE TO RELATED APPLICATIONS

The present patent application is a continuation-in-part of co-pending U.S. patent application Ser. No. 12/115,629 filed May 6, 2008 and entitled "Retinal Melatonin Suppressor", which prior application claims priority from and the benefit of U.S. Provisional Patent Application No. 61/026,905 filed Feb. 7, 2008 and entitled "Light Wavelength Conditioning Optical Device", the entirety of which prior applications are incorporated herein by this reference.

FIELD OF THE DISCLOSURE

This disclosure relates to a retinal melatonin suppressor, eyewear, an optical treatment system capable of suppressing melatonin found in the retina, and a coating capable of giving a lens on which the coating is applied retinal melatonin suppression properties. More specifically, this disclosure relates to the use of photoluminescent material with nanocrystals capable of emitting desirable light at specific wavelengths in the direction of the retina.

BACKGROUND

Darwinian theory states that humans evolved on Earth and are consequently adapted to interact with their environment. For example, when exposed to sunlight, human skin synthesizes vitamin D, a useful vitamin. The use of blue light (i.e., the color of the sky), when used in conjunction with an aminolevulinic acid treatment, is documented to improve porphyrin response times in skin.

The human eye is another organ known to react to environmental factors. Phototherapy, or the science of exposing the body to a spectrum of light for therapeutic purposes, is known or believed to be effective in treating Seasonal Affective Disorder, nonseasonal depressions, and delayed sleep phase syndrome when specific types of light are received by the human eye.

The first generation of light therapy devices produced a white light across the spectrum of wavelength, often requiring a source to illuminate at levels of up to 10,000 lux. Such intense light includes ultraviolet and infrared light that can be harmful to the human eye at intense levels. The benefit from these devices is cancelled by these adverse health benefits associated with intense levels of exposure.

Modern studies reveal that certain specific wavelengths of light, often in the blue spectrum ranging from 420 to 485 nm, are most effective in the treatment of Seasonal Affective Disorder and other psychiatric conditions. These benefits have been linked with the capacity of blue light to suppress the naturally present melatonin in the human retina, and more specifically, to interact with the melatonin receptor 1B (MT2 subtype). Melatonin is a primary hormone secreted by the pineal gland. Other research has shown a greater proportion of melatonin in the inferior and/or nasal portion of the retina.

Figure 1:
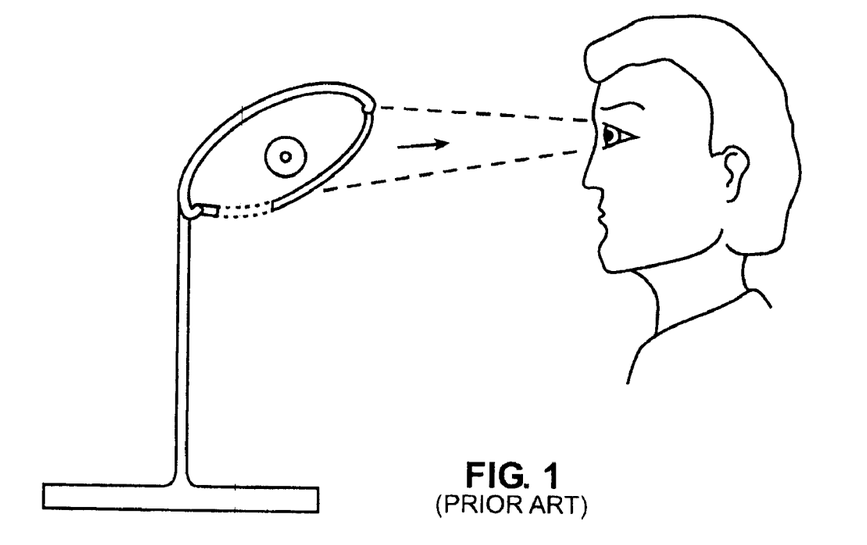
FIG. 1 is a figurative illustration of a nonportable light therapy device from the prior art.

Existing cosmetic devices that seek to expose individuals to light at wavelengths in the blue spectrum are bulky and difficult to manage. In addition, such devices require a power source and are otherwise difficult or impossible to use in a mainstream consumer application. An example of a prior art device is shown in FIG. 1. A selective color filter is placed between a nonportable source of light and a user of the device. Since the effective dose is measured as the incoming flux of radiation multiplied by the exposure time to the radiation, for a constant dose, the time of exposure can only be reduced if the intensity of the light is increased. As a consequence, the benefits of high-intensity light, even in the blue spectrum, is offset by the potential health hazards from intense light exposure.

Figure 2:
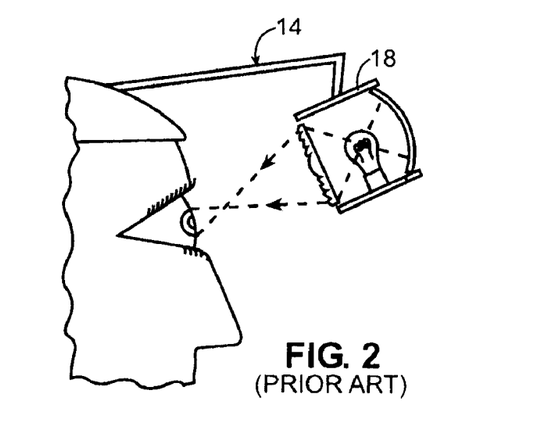
FIG. 2 is a figurative illustration of a portable light therapy device from the prior art.

In addition, most existing light therapy devices make use of an electric power source to generate light. Some models of light enhancement devices include eyewear with battery-powered light emitting diodes (LEDs) or other light sources. An example of this prior art device is shown in FIG. 2. Glasses equipped with bulky equipment are uncomfortable to wear and require frequent regeneration of the power source. While these devices convey the benefits of light therapy in the strictest sense, they do not address the real challenges inherent with the cosmetic and practicality concerns of the wearer.

Yet another type of prior art sunglasses used for light therapy does not use a power source but simply filters and attenuates incoming ambient photons at sunlight spectrum wavelengths. This technology makes use of a filter or a plurality of filters to eliminate or otherwise attenuate part of the incoming light spectrum (often, any non-beneficial wavelengths) from passing through the medium. In short, such technology is subtractive only and does not enhance beneficial wavelengths.

Finally, another type of prior art uses chemically fluorescent material to enhance the sensation of certain specific colors in the visible spectrum by use of a fluorescent dye. As a consequence of dyeing the lens, other colors in the visible radiation spectrum decrease in intensity. A contrast is created and some colors that cannot be perceived by color challenged individuals, for example blue, appear brighter. This system does not increase the incoming flux of any single color; it merely segregates a problematic spectrum from the overall spectrum to facilitate differential perception.

It would therefore be advantageous to provide a cosmetically acceptable, wearable device that increases the exposure of all or part of the human retina to beneficial wavelengths of light without requiring the use of bulky devices, power sources, or high-intensity fluxes. In particular, it would be advantageous to provide a solution that can be both subtractive and additive-converting nontherapeutic (or possibly even harmful) wavelengths into therapeutic, beneficial, or at the very least, nonharmful wavelengths.

SUMMARY

This disclosure relates to the application to an optical device of a photoluminescent material with a plurality of nanocrystals, such as quantum dots or other fluorescent nanoparticles, each capable of absorbing photons at a first (potentially undesirable) wavelength and emitting the absorbed energy at a second, desired wavelength. By directing, for example, emitted blue light in the direction of a human retina, naturally occurring melatonin may be suppressed. The disclosure also contemplates the placement of nanocrystals over the entire surface of a lens or a portion of a lens to optimize the melatonin exposition to the desired wavelength while reducing overall luminescence. Nanocrystals can be applied as a coating, as part of a material applied to the lens, either superficially or within the lens, as part of eyewear, or even as an optical treatment system.

In another embodiment, the photoluminescent material is placed on a lens along with a filter layer selected and configured to attenuate at least a portion of the desired or selected wavelengths of light emitted by the photoluminescent material. The filter layer may be configured so as to provide spatially differential attenuation of the selected wavelengths. For example, the attenuation of the filter layer (which may comprise, for example, a coating applied to a surface of the lens or a dye that is allowed to permeate the substrate forming the lens) may gradually increase in a direction from superior to inferior portions of the lens, and/or in a direction from a temporal to a nasal portion of the lens. In this manner, application of the selected wavelengths of light to desired portions of the retina may be readily controlled, while still providing ease of manufacture.

BRIEF DESCRIPTION OF THE DRAWINGS

Certain embodiments are shown in the drawings. However, it is understood that the present disclosure is not limited to the arrangements and instrumentality shown in the attached drawings.

DETAILED DESCRIPTION

For the purposes of promoting and understanding the principles disclosed herein, reference is now made to the preferred embodiments illustrated in the drawings, and specific language is used to describe the same. It is nevertheless understood that no limitation of the scope of the invention is hereby intended. Such alterations and further modifications of the illustrated devices and such further applications of the principles disclosed and illustrated herein are contemplated as would normally occur to one skilled in the art to which this disclosure relates.

Certain materials have the property of being able to receive and absorb, at least temporarily, electromagnetic energy at a first profile of wavelengths or bands of wavelengths and to emit the electromagnetic energy at a second, different profile of wavelengths or bands of wavelengths. Dyes having fluorescence properties, such as known organic compounds, emit light close to or about the same wavelength as the light that has been absorbed. The emission profile of the light remains within 20 to 30 nm of the absorption profile. For example, some fluorescent dyes absorb red light and emit light somewhat shifted in the red direction. As a consequence, there can be no significant enhancement of any color of light because the absorbed light corresponds to the emitted light.

Figure 4:
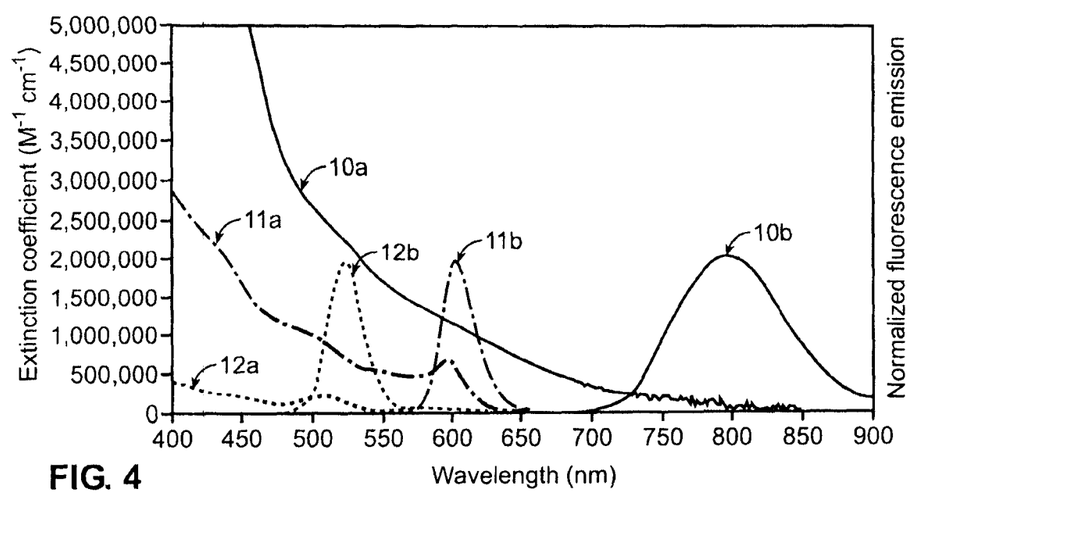
FIG. 4 is a graphical representation of the absorption and emission profiles of three different examples of nanocrystals as shown in FIG. 3 according to an embodiment of the present disclosure.

Nanocrystals differs greatly from fluorescent dyes in their absorption and emission profiles. FIG. 4 shows the difference between the absorption and emission profiles for three different types of nanocrystals. Absorbed light is stored from significantly lower wavelengths and emitted at very narrow bands—a red-emitting nanocrystal does not absorb red light, and as a consequence, light enhancement at a specific wavelength is possible.

Figure 3:
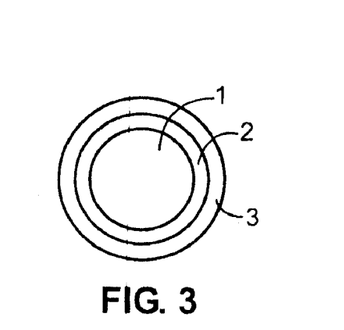
FIG. 3 is a diagrammatical representation of nanocrystals according to an embodiment of the present disclosure.

FIG. 4 shows three possible photoluminescent materials with nanocrystals, such as so-called quantum dots as shown in FIG. 3, having different absorption and emission profiles for the visual spectrum of wavelengths. As known in the art, quantum dots, such as those manufactured by Invitrogen Corporation and shown in FIG. 3, may comprise a small core 1 of a semiconductor material such as cadmium with selenium or tellurium within an outer shell 2 also of a semiconductor material such as zinc sulfide that is itself surrounded with a suitable polymer 3 such as polyethylene glycol (PEG). The emission color of a quantum dot is a function of its size, which typically ranges from 10 to 20 nm in diameter. In a similar vein, so-called "Cornell Dots" may also be employed. As described in U.S. Patent Application Publication Nos. 2004/0101822 (published May 27, 2004) and 2006/0183246 (published Aug. 17, 2006), the entirety of which are incorporated herein by this reference, Cornell Dots comprise a similar core and shell arrangement as quantum dots on the same dimensional scale, but in which the core comprises a few molecules of fluorescent dye surrounded by a silica shell without the additional polymer coating.

In FIG. 4, lines 10a, and 10b respectively illustrate the photoluminescent absorption and emission profiles for the black Qdot® nanocrystal from the Invitrogen Corporation, which appears black because it emits light at a wavelength of about 800 nm. Lines 11a, and 11b respectively illustrate the photoluminescent absorption and emission profiles for the orange Qdot® nanocrystal from Invitrogen Corporation, which appears orange because it emits light at a wavelength of about 605 nm. Finally, lines 12a, and 12b respectively illustrate the photoluminescent absorption and emission profiles for the blue Qdot® nanocrystal from Invitrogen Corporation, which appears blue because it emits light at a wavelength of about 525 nm. In a presently preferred embodiment, photoluminescent materials (such as nanocrystals) that emit substantially light tending toward the blue portion of the visible spectrum are employed.

FIG. 4 illustrates how shorter wavelengths shown to the left of the figure are absorbed and then emitted at a different, longer wavelength. While one type and model of nanocrystals using quantum dot technology is shown and disclosed, the use of any type of nanocrystals capable of absorption at one portion of the wavelength spectrum and the release of energy at a selected visible wavelength such as, for example, blue, is contemplated.

As noted above, blue light at specific wavelengths has been found useful in treating Seasonal Affective Disorder at low-intensity exposure. Light, often quantified as "blue light" having a wavelength ranging between 460 to 485 nm, may be efficient in treating photosensitive pigments with a peak sensitivity of about 479 nm. While a preferred embodiment with the emission of photons as between 420 to 485 nm is disclosed, emission at other wavelengths in the visible, near visible, or invisible spectrum is also contemplated.

For example, in one embodiment, invisible ultraviolet (UV) wavelengths are converted into visible blue or green wavelengths. Of course, other wavelength conversion may be possible based on the type and/or capabilities of the particular photoluminescent (or conversion) material used. More particularly, quantum or Cornell dots are added to optical devices, such as lenses, during manufacturing. Such lenses may be incorporated into eyewear, which may in turn be incorporated into a treatment systems, as described below.

Figure 5A:
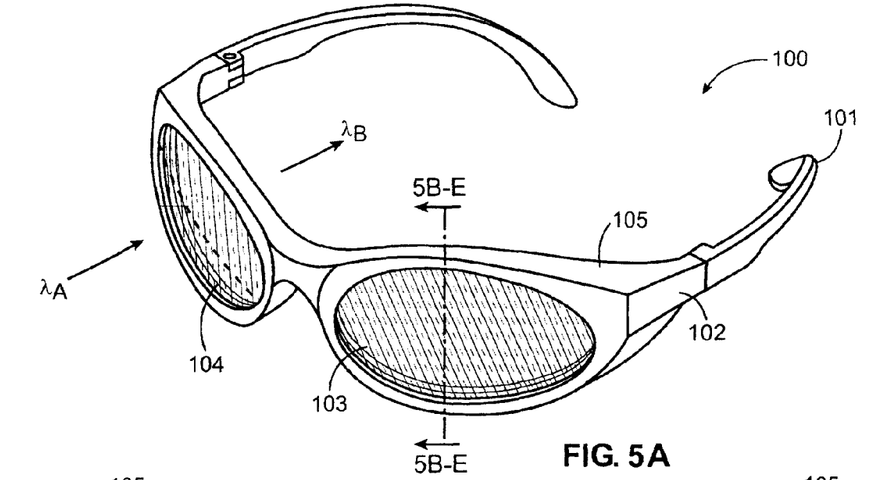
FIG. 5A is a perspective view of eyewear equipped with optical lenses where substantially all of at least one lens includes a photoluminescent material according to an embodiment of the present disclosure.

FIG. 5A illustrates a retinal melatonin suppressor 100 in the form of eyewear having at least one lens 103, 104 and a photoluminescent material including nanocrystals (as shown, for example, in FIG. 3) applied to substantially all of each lens 103, 104 to emit photons at a selected wavelength, $\lambda_B$, in the direction of a retina of a wearer of the suppressor 100 in response to incoming or source light, $\lambda_A$. Thus, the light provided to the wearer's retina comprises the emitted light, $\lambda_B$, plus that portion of the incoming light, $\lambda_A$, that is not blocked by the lens 103 or absorbed by the nanocrystals. Note that, although both lenses 103, 104 are illustrated as having the photoluminescent material applied essentially identically, this is not a requirement and the photoluminescent material may be applied differently to each lens 103, 104. Each lens 103, 104 can be any optical device used to pass light on to, or focus light into, the eyes of a wearer including but not limited to a corrective lens, a sunglass lens, a monocular or binocular lens, etc. In the illustrated embodiment, the suppressor 100 includes a wearable frame 105, with handles 101 connected by a pivot 102 with the frame 105 and at least one optical lens 103 supported by the wearable frame (also as 104). As best shown in FIGS. 5B-5E, each of the at least one lens 103, 104 in the illustrated embodiment includes a substrate 107 that is substantially transparent to at least a portion of the visible light spectrum and a photoluminescent material 108, 109, 208 applied to the substrate 107 that emits electromagnetic energy of at least a selected wavelength, $\lambda_B$, after being exposed to a source spectrum of electromagnetic energy, $\lambda_A$.

Figure 5B:
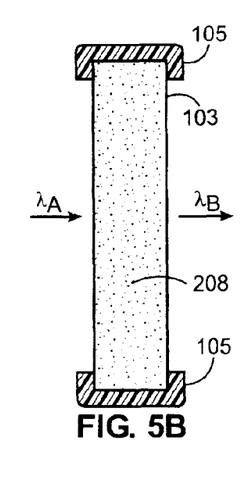
FIG. 5B is a cross-sectional view along line 5B-E as shown in FIG. 5A where the substrate uniformly includes the photoluminescent material.
Figure 5C:
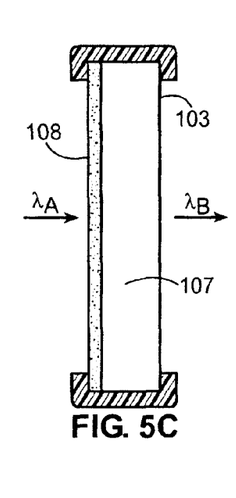
FIG. 5C is a cross-sectional view along line 5B-E as shown in FIG. 5A where a layer of photoluminescent material is located on an external surface of the substrate.
Figure 5D:
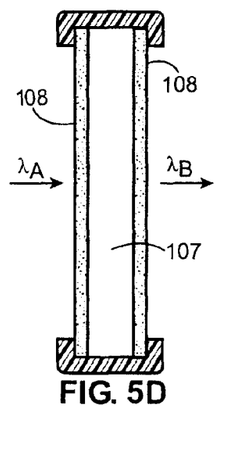
FIG. 5D is a cross-sectional view along line 5B-E as shown in FIG. 5A where a layer of photoluminescent material is located on both an internal and external surface of the substrate.
Figure 5E:
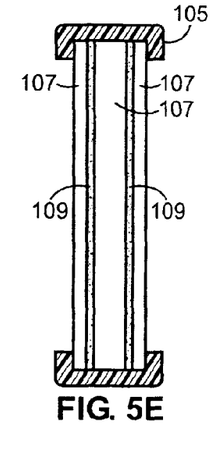
FIG. 5E is a cross-sectional view along line 5B-E as shown in FIG. 5A where two layers of photoluminescent material are sandwiched in the substrate.

Furthermore, FIGS. 5B-5E illustrate different techniques whereby the photoluminescent material may be applied to substrate 107. In FIG. 5B, the photoluminescent material 208 is more or less uniformly distributed throughout the substrate, which may be achieved through any suitable process for impregnating or dyeing the substrate material with the photoluminescent material. Alternatively, as shown in FIGS. 5C and 5D, the photoluminescent material 108 can be applied as a layer to either or both of an external surface (i.e., facing incident light) or an internal surface (i.e., in the direction of the emitted light) of the substrate 107, although an embodiment applied to only the internal surface is not shown. Further still, as illustrated in FIG. 5E, the photoluminescent material 109 may be non-uniformly distributed within the transparent substrate 107. For example, as shown in FIG. 5E, one or more layers of the photoluminescent material 109 are coated on inner surfaces of the substrate 107 in a sandwich-like structure. The layers illustrated in FIGS. 5C-5E may be created using any suitable deposition technique, such as dielectric coating, spray or spin coating, sputtering, diffusion into the substrate, the use of a polymer sheet attached via electrostatic force, the use of a polymer sheet attached via a layer of adhesive, the use of multiple substrate layers each having internal layers that are subsequently laminated together, etc.

Figure 6A:
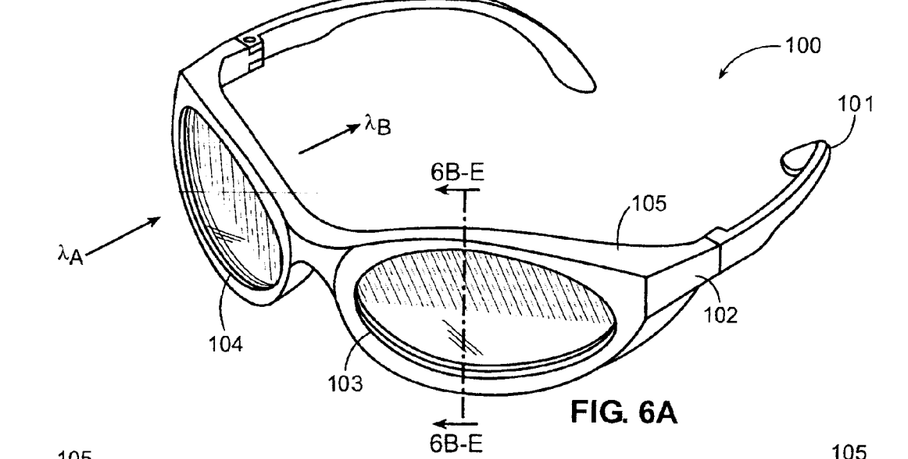
FIG. 6A is a perspective view of eyewear equipped with optical lenses where only a portion of at least one lens includes photoluminescent material according to another embodiment of the present disclosure.
Figure 7A:
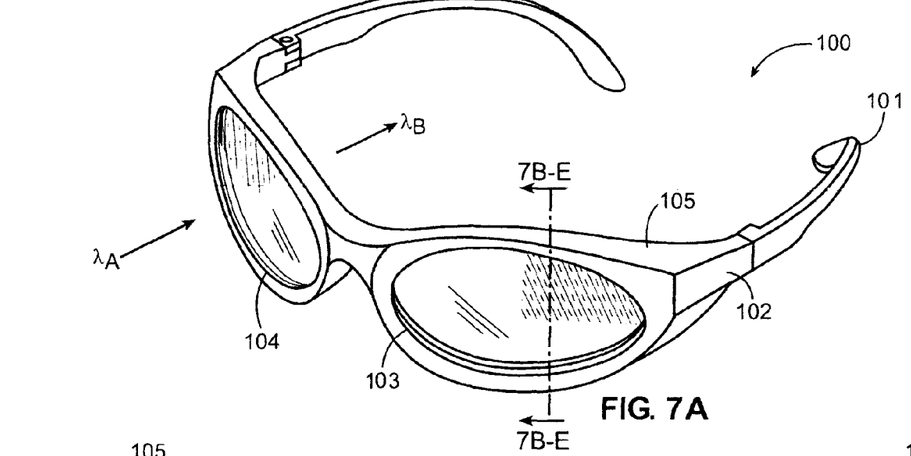
FIG. 7A is perspective view of eyewear equipped with optical lenses where another portion of at least one lens includes photoluminescent material according to yet another embodiment of the present disclosure.

Although the suppressor 100 illustrated in FIG. 5A is illustrated in an eyewear embodiment (i.e., including a the frame 105, etc.), it will be appreciated that the suppressor 100 may comprise a stand-alone optical device, such as a contact lens or unmounted lens. It is further noted that any of the optical devices described herein (including, for example, the lenses 103, 104 as shown in FIGS. 5A, 6A, and 7A) can be made of any material known to be used in the production of optical devices and to which the photoluminescent material 108, 109, 208 can be applied, including but not limited to glass, plastic, polycarbonate, polyurethane, and TRIVEX™ lens material. Regardless of the material used, various properties of the substrate material may be exploited according to various embodiments described herein. For example, if the substrate material is glass, and such type of glass has (or is otherwise treated or modified to have) ultraviolet (UV) blocking properties, the emitted light, $\lambda_B$, would not include UV light (or at least substantially attenuated UV light) because this light must pass through the substrate 107. Thus, the UV light that would otherwise be blocked by the substrate material can be used beneficially as the source of blue light if the layer of photoluminescent material with nanocrystals is placed on the external surface of the substrate as shown, for example, in FIG. 5C and is capable of transforming UV light into visible light that can be transmitted through the substrate material.

The human eye is equipped with a natural shutter called the pupil that controls the amount of light coming into the eye and, consequently, incident upon the retina. As intensity of incident light upon the retina increases, the pupillary reflex causes the pupil to constrict thus diminishing the incidence of all light, including beneficial light, incident upon the retina. In the context of the instant disclosure, this reflex could diminish the otherwise beneficial light emitted by the photoluminescent material. Thus, it may be desirable to provide the photoluminescent material on only a portion of an optical device such that the overall perceived irradiance is not increased to the point that the pupillary reflex negates or attenuates any beneficial effect. For example, by selecting certain portions of the lens 103 on which to include photoluminescent material, the effective incoming emitted light on the retina may be improved because the pupil does not constrict.

Furthermore, research has shown that melatonin distribution on the retina is not uniform and more therapeutic light may be most beneficial when applied to that portion of the retina with more photoreceptors. As known in the art, the visual field perceived by the brain is actually inverse to the structure of the retina. That is, for example, light entering from above the eye is actually projected onto the inferior portion of the retina, whereas light entering from the temporal side of the eye is actually projected onto the nasal portion of the retina. Thus, in one contemplated embodiment, a portion of the optical device with photoluminescent material is such that light emitted therefrom passes through the pupil to a nasal portion and/or inferior portion of the retina. In other embodiments, other techniques may be used to direct a portion of the emitted light from the optical device onto a specific portion of the retina through the pupil. For example, a portion of the lens 103 can be adapted at a different flat angle or concave angle to specifically direct incoming light. Examples of such embodiments are further illustrated with respect to FIGS. 6A-6E and 7A-7E. In particular, FIG. 6A shows eyewear 100 where the photoluminescent material is applied only to a first portion of the lenses 103, 104, e.g., to the upper half of the lenses 103, 104. Alternatively, FIG. 7A shows eyewear 100 where the photoluminescent material is applied only to a second, smaller portion of the lenses 103, 104, e.g., to the upper temporal quadrant of the lenses 103, 104. Once again, it is noted that the lenses 103, 104 in the embodiments shown in FIGS. 6A and 7A do not necessarily need to be equivalent in terms of application of the photoluminescent material.

Figure 6B:
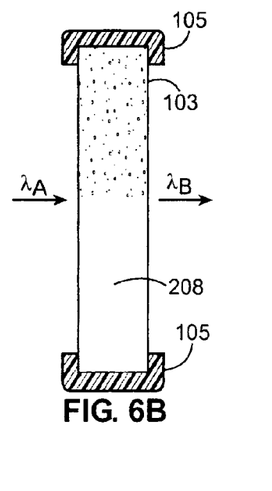
FIG. 6B is a cross-sectional view along line 6B-E as shown in FIG. 6A where the portion of the substrate uniformly includes the photoluminescent material.
Figure 6C:
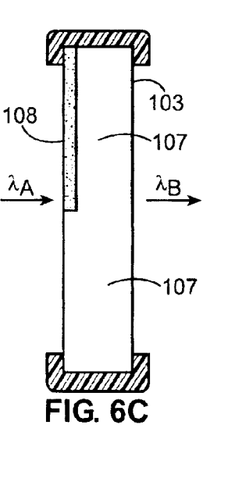
FIG. 6C is a cross-sectional view along line 6B-E as shown in FIG. 6A where a layer of photoluminescent material is located on an external surface of the substrate.
Figure 6D:
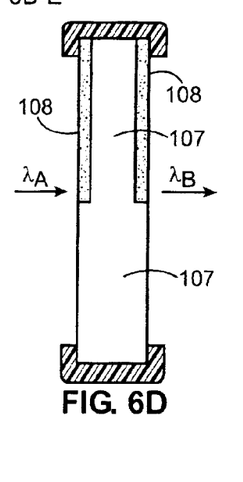
FIG. 6D is a cross-sectional view along line 6B-E as shown in FIG. 6A where a layer of photoluminescent material is located on both an internal and external surface of the substrate.
Figure 6E:
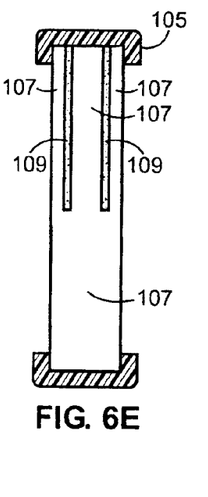
FIG. 6E is a cross-sectional view along line 6B-E as shown in FIG. 6A where two layers of photoluminescent material are sandwiched in the substrate.
Figure 7B:
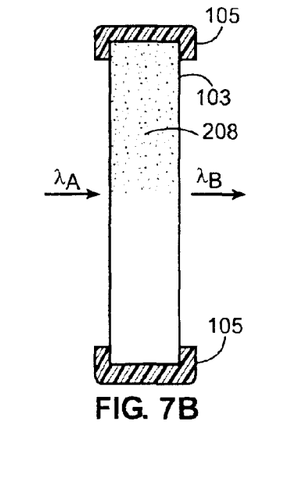
FIG. 7B is a cross-sectional view along line 7B-E as shown in FIG. 7A where the other portion of the substrate uniformly includes the photoluminescent material.
Figure 7C:
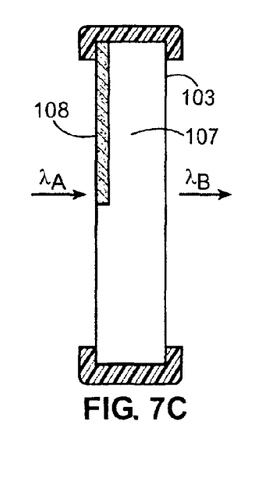
FIG. 7C is a cross-sectional view along line 7B-E as shown in FIG. 7A where a layer of photoluminescent material is located on an external surface of the substrate.
Figure 7D:
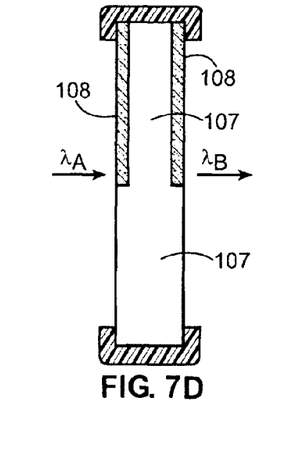
FIG. 7D is a cross-sectional view along line 7B-E as shown in FIG. 7A where a layer of photoluminescent material is located on both an internal and external surface of the substrate.
Figure 7E:
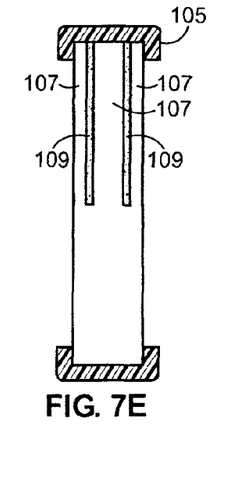
FIG. 7E is a cross-sectional view along line 7B-E as shown in FIG. 7A where two layers of photoluminescent material are sandwiched in the substrate.

FIGS. 6B-6E and 7B-7E are taken along the cut line shown in FIGS. 6A and 7A, respectively, and illustrate the lens 103 as mounted in the frame 105. Note that the embodiments illustrated in FIGS. 6B-6E and 7B-7E are essentially the same as those illustrated in FIGS. 5B-5E, with the exception of the extent (i.e., the area or portion of the substrate) to which the photoluminescent material 108, 109, 208 is applied to the substrate 107. As shown in FIGS. 6B and 7B, the photoluminescent material with nanocrystals 208 is uniformly distributed throughout the substrate, whereas in FIGS. 6C and 7C, the photoluminescent material with nanocrystals is placed as a coated outer layer 108 on an upper external surface of the transparent substrate 107. In another embodiment (not shown), the layer is only placed as a internal layer on an upper internal surface of the transparent substrate 107. FIGS. 6D and 7D illustrate two upper layers 108 with nanocrystals placed as both an external layer and an internal layer 108 on both the external and internal surfaces of the substrate 107. As shown in FIGS. 6E and 7E, one or more layers having photoluminescent material 109 are sandwiched within the transparent substrate 107, as described previously. Once again, the deposition techniques described above may be employed when applying the photoluminescent material to the lenses 103, 104 as shown in any of the embodiments illustrated in FIGS. 6B-6E and 7B-7E.

While various different configurations are shown as FIGS. 5A-5E, 6A-6E and 7A-7E, other possible configurations are contemplated. By way of a nonlimiting example, the use of clip-on lenses, the treatment by an incoming light exposing only part of the lens, and the use of additional light attenuating/blocking coatings in addition to the nanocrystal layer(s) are also contemplated.

In another embodiment, an optical treatment system is contemplated with a source such as a lamp, LED(s) or other light source (illustrated for its radiation as $\lambda_A$) to emit a source light having a desired spectrum. The system further includes an optical device such as the above-described lens 103 having a photoluminescent material applied to the lens 103 (for example, as described in any of the embodiments discussed above) to emit photons responsive to the source spectrum. In a preferred embodiment, the source spectrum includes invisible and near-visible UV light.

In yet another embodiment, the benefits described above may be provided with a separately-provided, potentially temporary coating for an optical device. For example, such coating may comprise a fixation matrix (such as a fluid, gel or other form having suitable viscosity to allow application of the coating to optical device, or being sufficiently flexible to be applied to a surface) and quantum dots of any desired concentration relatively uniformly suspended within the matrix. For example, in one embodiment, the fixation matrix may comprise a flexible polymer substrate that adheres to the optical device via electrostatic forces or a suitable adhesive. In another embodiment, the fixation matrix may include a transport fluid or gel for adhesion onto an optical device after stabilization on the optical device. For example, the fixation matrix may comprise a liquid form that, when sprayed on an optical device, dries to form a coating on the lens 103. As with the previously described embodiments, incident light on the coating causes the emission of photons at a desired wavelength range, e.g., 420 to 485 nm in response to invisible or near-visible UV light.

In further alternative embodiments, described below with reference to FIGS. 8-11, the photoluminescent material (as described above) is applied to a lens along with a filter layer that is configured to attenuate at least a portion of the selected wavelengths emitted by the photoluminescent material. In this alternative embodiment, the filter material is provided to spatially differentiate the amount of the selected wavelengths passed through the lens, thereby providing greater control over the application of the selected wavelengths.

Figure 8A:
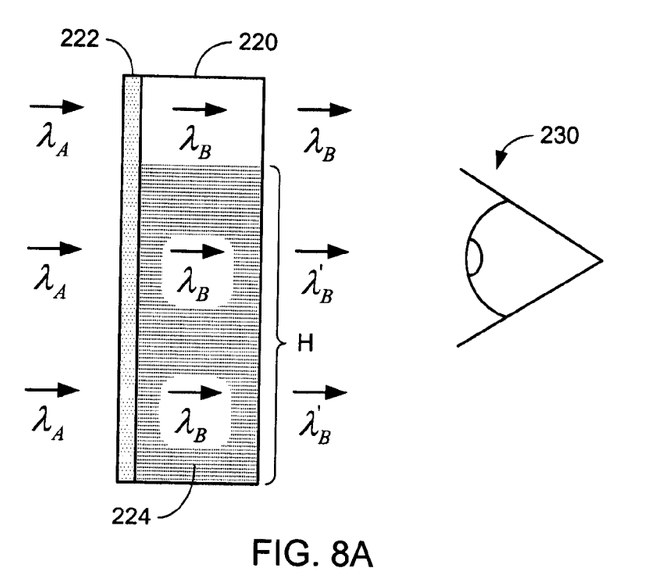
FIGS. 8A-8C are cross-sectional schematic views of a lenses comprising photoluminescent material and filtering material in accordance with an alternative embodiment.

Referring now to FIG. 8A, a schematic cross-sectional view of a lens in accordance with the alternative embodiment is shown. In particular, the lens comprises a substrate 220 (comprising any of the above-mentioned materials) having applied thereto photoluminescent material 222 as well as filtering material 224. Generally, the photoluminescent material 222 and filtering material 224 are applied to the substrate 220 in any manner such that the selected wavelengths, $\lambda_B$, emitted by the photoluminescent material 222 are at least partially attenuated by the filter material 224. In this manner, the amount/amplitude of the selected wavelengths reaching an eye 230 of a user (and, consequently, the retina of the user) may be more finely controlled. For example, the filtering material may comprise any of a number of suitable dyes used to dye the substrate 220, as known to those having ordinary skill in the art. In one embodiment in which the selected wavelengths are generally in the blue light wavelengths, the filtering material 224 may comprise Ciba-Geigy Orasol Orange G dye used to dye lenses as described in U.S. Pat. No. 4,952,056, the teachings of which are incorporated herein by this reference. In the embodiment illustrated in FIG. 8A, the photoluminescent material 222 covers substantially the entire forward (or external) surface of the substrate 220. In this manner, the resulting light at the selected wavelengths is emitted in a substantially uniform manner, as shown. However, as noted above, the photoluminescent material 222 may instead be applied to only a portion of the forward surface or, as illustrated in FIGS. 5D and 5E for example, in alternate configurations relative to the substrate 220. Furthermore, although the photoluminescent material 222 is illustrated in FIG. 8A as an additional layer applied to the forward surface of the substrate 220, as noted above, it may be possible to diffuse or otherwise permeate the photoluminescent material 222 within the substrate 220, or to place the photoluminescent material on another surface of the substrate 220. Further still, although the photoluminescent material 222 is shown having a substantially uniform thickness and/or density, this is not a requirement as the photoluminescent material 222 could be applied in varying thicknesses and/or densities.

As further illustrated in FIG. 8A, the filter material 224 is applied to the substrate 220 such that a portion of the emitted selected wavelengths of light is attenuated thereby. In the illustrated embodiment, the filter material 224 permeates the substrate 220 throughout an inferior portion, H, of the substrate whereas the remaining superior portion of the substrate 220 does not include the filter material. Such a configuration is readily achievable, as known in the art, through dyeing processes in which the substrate 220 is dipped in an appropriate dye and allowed to diffuse through the substrate. Once again, although the filter material 224 is illustrated as being distributed in a substantially uniform manner throughout the entirety of that portion of the substrate 220 in which it is embedded, those having skill in the art will appreciate that this is not a requirement and that that filter material 224 may be distributed throughout the relevant portion of the substrate 220 in a non-uniform manner according to any desired gradient profile. In this manner, non-uniform attenuation of the emitted selected wavelengths may be achieved as illustrated in FIG. 8A. As shown, along the superior portion of the substrate 220, the emitted selected wavelengths are allowed to pass through the substrate 220 in substantially unattenuated form, $\lambda_B$ (ignoring, for purposes of this description, any internal reflections arising at the interfaces of either the forward or the rearward surface of the substrate 220 and the surrounding environment), whereas those portions of the emitted selected wavelengths passing through the inferior portion of the substrate 220 and the filter material 224 emerge in an attenuated form, $\lambda'_B$. As noted above, given the manner in which an eye 230 inversely projects the field of view upon the retina, this result in proportionately higher levels of the selected wavelengths impinging upon the inferior portion of the retina.

Figure 8B:
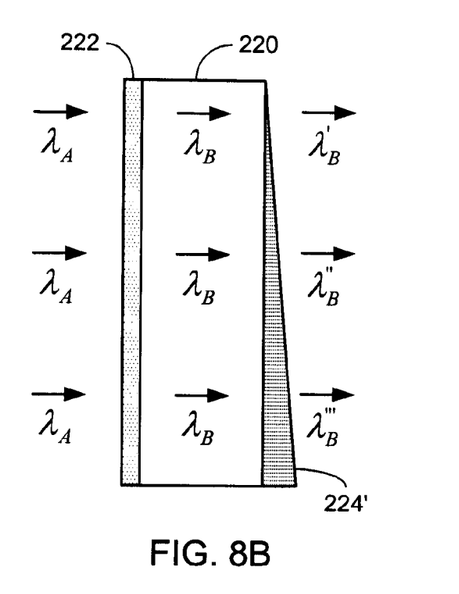
Figure 8C:
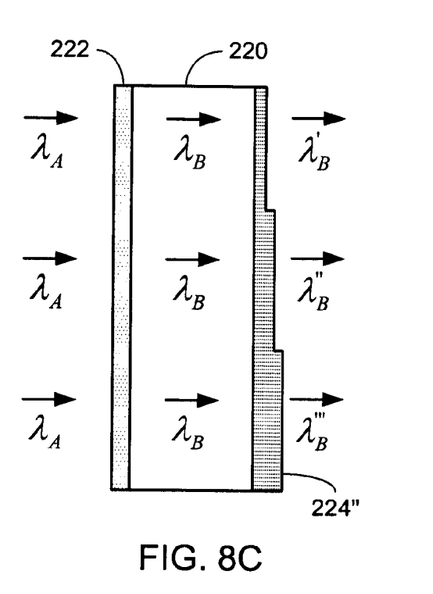

FIGS. 8B and 8C illustrate further variations of the alternative embodiment in which the filter materials 224', 224" (i) are applied to the rearward (or internal) surface of the substrate 220 and (ii) comprise examples of gradient profiles. In these instances, the filter material 224', 224" is applied as a coating to establish a separate layer on the rearward surface of the substrate 220. The gradient profiles of the filtering material causes a spatial differentiation of the attenuation of the selected wavelengths. In the example illustrated in FIG. 8B, the filtering material 224' is arranged according to a substantially continuous increasing gradient in a superior to inferior direction. As a result, the transmitted portions of the selected wavelengths are continuously attenuated to increasing degrees from the superior to inferior portions of the substrate 220, i.e., $|\lambda'_B| > |\lambda''_B| > |\lambda'''_B|$. In the example illustrated in FIG. 8C, the filtering material 224" is arranged according to an increasing stepwise gradient, again in a superior to inferior direction. In this case, attenuation of the selected wavelengths will likewise occur in a stepwise fashion. As will be appreciated by those having ordinary skill in the art, such stepwise grading of the filtering material may be similarly achieved in the embedded embodiment illustrated in FIG. 8A by varying the concentration of the filtering material 224 embedded within substrate 220 in stepwise fashion.

Figure 9A:
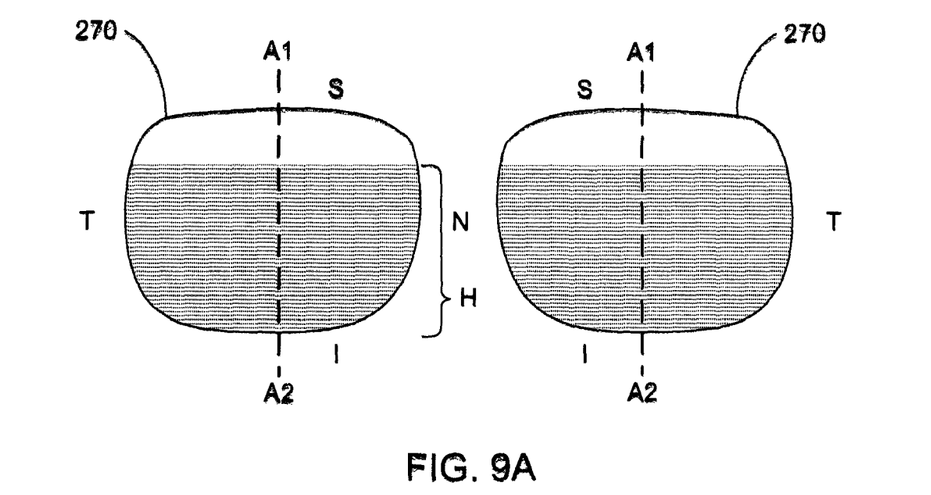
FIG. 9A is an elevational view of a first example of a pair of lenses in accordance with the alternative embodiment.
Figure 9B:
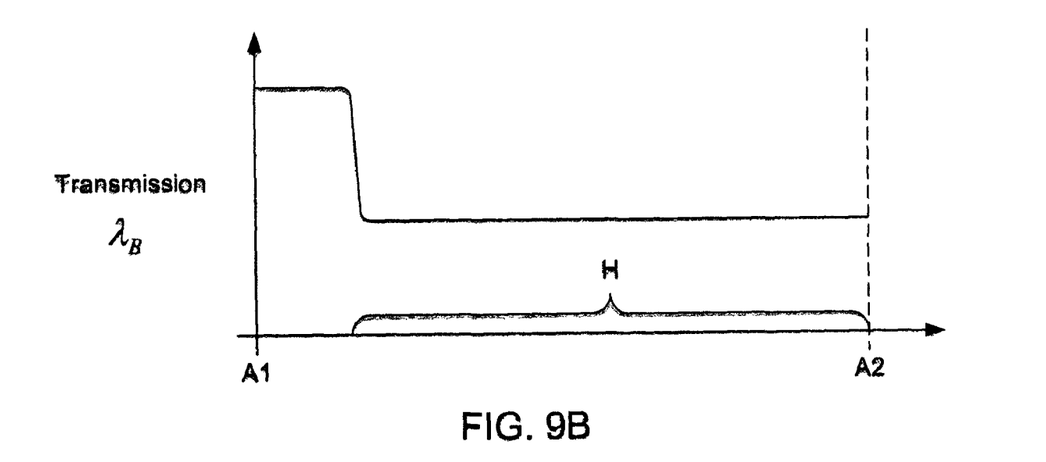
FIG. 9B is graphical representation of a transmission profile of the lenses illustrated in FIG. 9A along the axis A1-A2 at an emitted wavelength of the photoluminescent material.
Figure 10A:
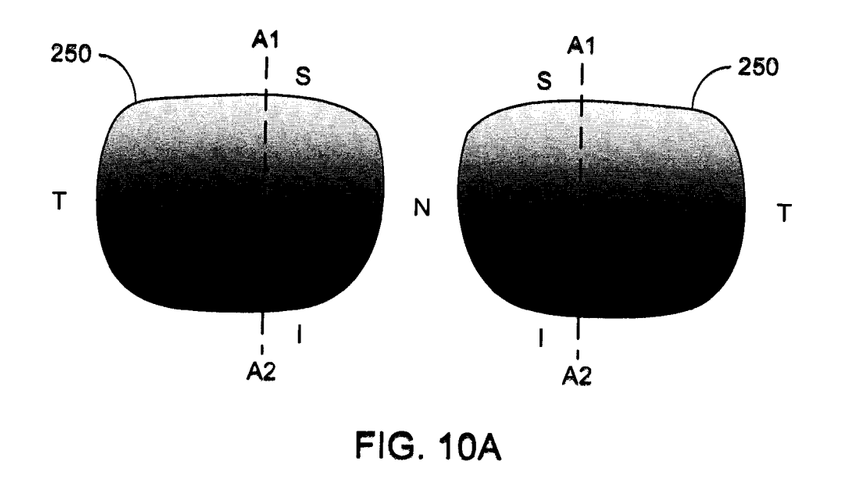
FIG. 10A is an elevational view of a second example of a pair of lenses in accordance with the alternative embodiment.
Figure 10B:
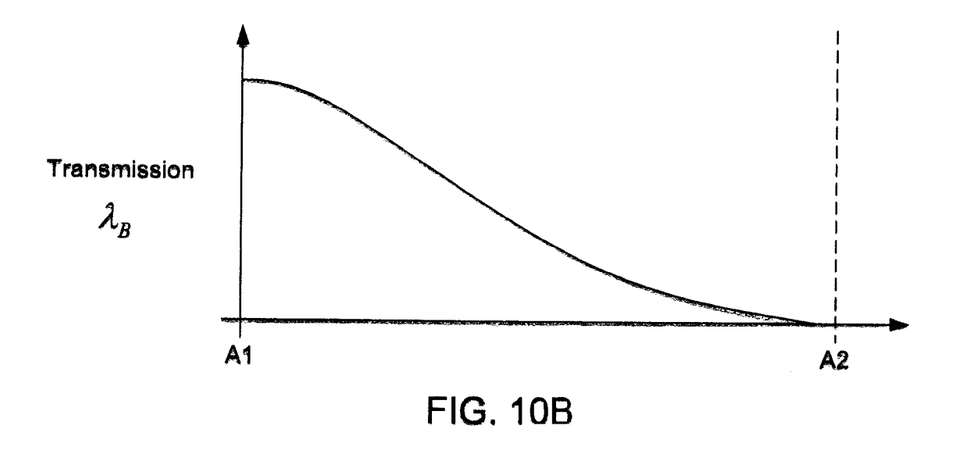
FIG. 10B is graphical representation of a transmission profile of the lenses illustrated in FIG. 10A along the axis A1-A2 at an emitted wavelength of the photoluminescent material.
Figure 11A:
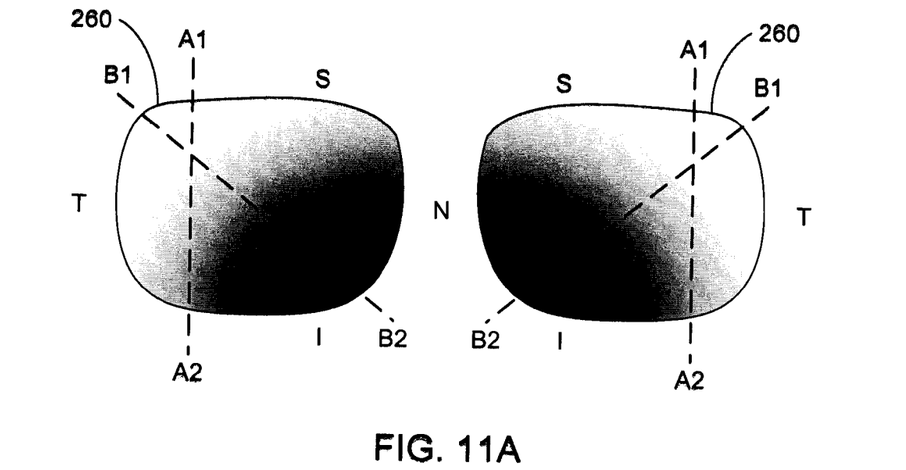
FIG. 11A is an elevational view of a third example of a pair of lenses in accordance with the alternative embodiment.
Figure 11B:
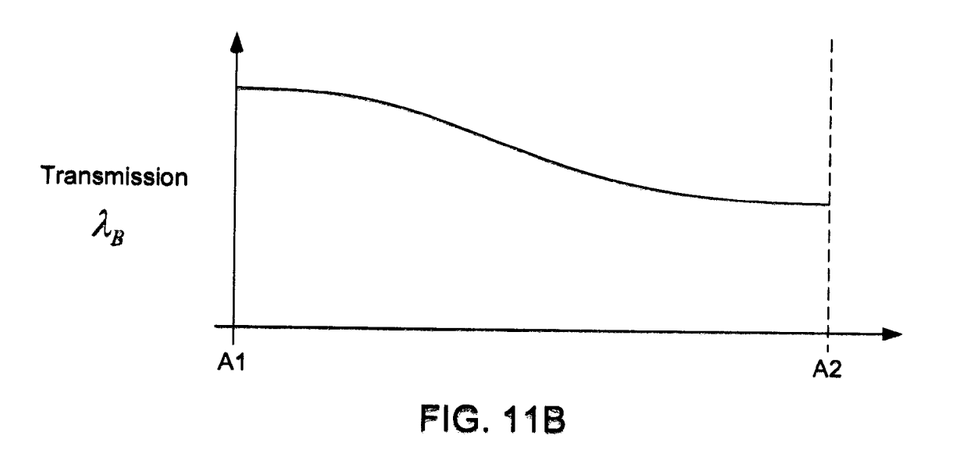
FIG. 11B is graphical representation of a transmission profile of the lenses illustrated in FIG. 11A along the axis A1-A2 at an emitted wavelength of the photoluminescent material.

Referring now to FIGS. 9-11, various examples of the alternative embodiment of FIG. 8 are now described. In particular, FIGS. 9A, 10A and 11A each illustrate an elevational view of the rearward surface (i.e., as they would be seen by a wearer thereof) of a pair of lens 250, 260, 270. Superior (S), inferior (I), temporal (T) and nasal (N) directions relative to each lens are indicated as shown. With regard to the embodiment of FIG. 9A, the filtering material (shaded region) is applied in a substantially uniform fashion in accordance with the example illustrated in FIG. 8A. As a result, transmission of the selected wavelength, $\lambda_B$, through the lenses 250 along the vertical axis A1-A2, for example, is as illustrated in FIG. 9B. As shown in FIG. 9B, transmission of the selected wavelengths is relatively high throughout the superior portion of lenses 250, whereas substantially uniform attenuation of the selected wavelengths results in the inferior portion of the lenses.

Referring to FIG. 10A, an embodiment is illustrated in which the filtering material (and, consequently, the attenuation of the selected wavelengths caused thereby) is applied to the lenses 260 according to a gradually increasing, vertically-oriented gradient profile, i.e., in a direction from superior portions to inferior portions of the lenses 260. In this embodiment, while the vertical gradient is gradually increasing, the filtering material is relatively uniformly applied along the horizontal breadth of the lenses 260, e.g., from the temporal to the nasal. The resulting transmission profile along vertical axis A1-A2, illustrated in FIG. 10B, reflects the gradual attenuation applied to the selected wavelengths from the superior to the inferior portions of the lenses 260. The embodiments illustrated in FIGS. 9A and 10A will result in relatively greater amounts/amplitudes of the selected wavelengths being applied to the inferior portions of the retina.

Figure 11C:
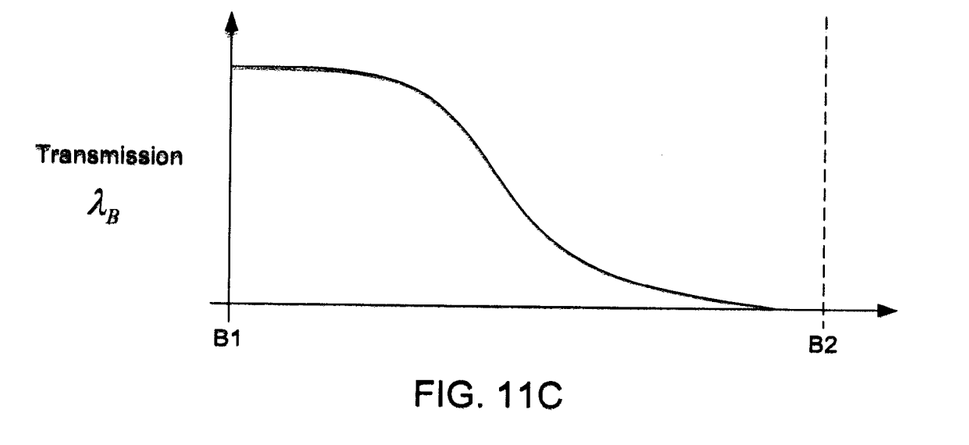
FIG. 11C is graphical representation of a transmission profile of the lenses illustrated in FIG. 11A along the axis B1-B2 at an emitted wavelength of the photoluminescent material.

Finally, with reference to FIG. 11A, an embodiment is illustrated in which the filtering material is applied to the lenses 270 according to gradually increasing, vertically-oriented and horizontally-oriented gradient profiles, i.e., in a direction from superior to inferior and from temporal to nasal portions of the lenses 270. The resulting transmission profile along vertical axis A1-A2, illustrated in FIG. 11B, reflects the gradual attenuation applied to the selected wavelengths from the superior to the inferior portions of the lenses 270, but also reflects the fact that the horizontal position of the vertical axis A1-A2, being closer to the temporal edge than the nasal edges of the lenses 270, results in relatively less attenuation of the selected wavelengths in the inferior portions of the lenses 270. In similar vein, transmission along the diagonal axis B1-B2, as illustrated in FIG. 11C, reflects the fact that transmission is highest at the superior temporal portions of the lenses 270, whereas transmission is lowest at the inferior nasal portions of the lenses 270. As a result, relatively greater amounts/amplitudes of the selected wavelengths will be applied to the inferior nasal portions of the retina.

It is understood that the preceding is merely a detailed description of some examples and embodiments of the present invention and that numerous changes to the disclosed embodiments can be made in accordance with the disclosure made herein without departing from the spirit or scope of the invention. For example, rather than strictly therapeutic implementations, the techniques and structures described above could be applied to a partially or purely cosmetic application. In such an application, the photoluminescent material could be applied in a manner to enhance the appearance of a wearer of, for example, eyewear configured as described above. The preceding description, therefore, is not meant to limit the scope of the invention but to provide sufficient disclosure to one of ordinary skill in the art to practice the invention without undue burden.

What is claimed is:

1. A retinal melatonin suppressor comprising:
   a lens;
   a photoluminescent material applied the lens to emit photons at a selected wavelength in at least a rearward direction relative to the lens; and
   a filter material applied to the lens to attenuate at least a portion of the photons at the selected wavelength emitted in the rearward direction.

2. The retinal melatonin suppressor of claim 1, wherein the photoluminescent material comprises nanocrystals.

3. The retinal melatonin suppressor of claim 2, wherein the nanocrystals are at least one of quantum dots or Cornell dots.

4. The retinal melatonin suppressor of claim 1, wherein the lens is an optical lens, a contact lens, a corrective lens, a sunglass lens, a monocular lens or a binocular lens.

5. The retinal melatonin suppressor of claim 1, wherein the selected wavelength is in a range of approximately 420 to 485 nm.

6. The retinal melatonin suppressor of claim 1, wherein the photoluminescent material is applied to at least a portion of a forward surface of the lens.

7. The retinal melatonin suppressor of claim 6, wherein the photoluminescent material is applied to substantially all of the forward surface of the lens.

8. The retinal melatonin suppressor of claim 1, wherein the filter material is applied to at least a portion of a rearward surface of the lens.

9. The retinal melatonin suppressor of claim 1, wherein the filter material permeates at least a portion of the lens.

10. The retinal melatonin suppressor of claim 1, wherein attenuation provided by the filter material is substantially spatially uniform.

11. The retinal melatonin suppressor of claim 1, wherein attenuation provided by the filter material increases in a direction from a substantially superior portion of the lens to a substantially inferior portion of the lens.

12. The retinal melatonin suppressor of claim 1, wherein attenuation provided by the filter material increases in a direction from a substantially temporal portion of the lens to a substantially nasal portion of the lens.

13. The retinal melatonin suppressor of claim 1, wherein the photoluminescent material is applied as a dielectric coating on the lens.

14. The retinal melatonin suppressor of claim 1, wherein the lens is made of a material selected from the group consisting of a glass, a plastic, a polycarbonate, a polyurethane, and TRIVEX™ lens material.

15. Eyewear comprising:
    a wearable frame; and
    the retinal melatonin suppressor of claim 1 supported by the wearable frame.

16. Eyewear comprising:
    a wearable frame; and
    at least one lens supported by the wearable frame, each of the at least one lens comprising a substrate that is substantially transparent to at least a portion of a visible light spectrum, a photoluminescent material applied to the substrate that emits electromagnetic energy of at least a selected wavelength after being exposed to a source spectrum of electromagnetic energy, and a filter material applied to the substrate to attenuate at least a portion of the electromagnetic energy at the selected wavelength.

17. The eyewear of claim 16, wherein the photoluminescent material comprises nanocrystals.

18. The eyewear of claim 17, wherein the nanocrystals are at least one of quantum dots or Cornell dots.

19. The eyewear of claim 16, wherein the at least one lens comprises an optical lens, a contact lens, a corrective lens, a sunglass lens, a monocular lens or a binocular lens.

20. The eyewear of claim 16, wherein the selected wavelength is in a range of approximately 420 to 485 nm.

21. The eyewear of claim 16, wherein the photoluminescent material is applied to at least a portion of a forward surface of each of the at least one lens.

22. The eyewear of claim 21, wherein the photoluminescent material is applied to substantially all of the forward surface of each of the at least one lens.

23. The eyewear of claim 16, wherein the filter material is applied to at least a portion of a rearward surface of each of the at least one lens.

24. The eyewear of claim 16, wherein the filter material permeates at least a portion of the substrate.

25. The eyewear of claim 16, wherein, for each of the at least one lens, attenuation provided by the filter material is substantially spatially uniform.

26. The eyewear of claim 16, wherein, for each of the at least one lens, attenuation provided by the filter material increases in a direction from a substantially superior portion of the lens to a substantially inferior portion of the lens.

27. The eyewear of claim 16, wherein, for each of the at least one lens, attenuation provided by the filter material increases in a direction from a substantially temporal portion of the lens to a substantially nasal portion of the lens.

28. The eyewear of claim 16, wherein the photoluminescent material is applied as a dielectric coating on each of the at least one lens.

29. The eyewear of claim 16, wherein the substrate comprises material selected from the group consisting of a glass, a plastic, a polycarbonate, a polyurethane, and TRIVEX™ lens material.

* * * * *